US011491319B2

(12) United States Patent
Merchant

(10) Patent No.: US 11,491,319 B2
(45) Date of Patent: Nov. 8, 2022

(54) MULTI-LINE OPPOSED INLET INFUSION COUPLING

(71) Applicant: Michael A. Merchant, Franklin, MA (US)

(72) Inventor: Michael A. Merchant, Franklin, MA (US)

(*) Notice: Subject to any disclaimer, the term of this patent is extended or adjusted under 35 U.S.C. 154(b) by 68 days.

(21) Appl. No.: 16/273,399

(22) Filed: Feb. 12, 2019

(65) Prior Publication Data

US 2019/0247643 A1 Aug. 15, 2019

Related U.S. Application Data

(60) Provisional application No. 62/629,919, filed on Feb. 13, 2018.

(51) Int. Cl.
| | |
|---|---|
| *A61M 39/10* | (2006.01) |
| *A61M 5/14* | (2006.01) |
| *A61J 1/10* | (2006.01) |
| *A61M 25/00* | (2006.01) |

(52) U.S. Cl.
CPC ........ *A61M 39/105* (2013.01); *A61M 5/1408* (2013.01); *A61J 1/10* (2013.01); *A61M 25/0097* (2013.01); *A61M 2206/20* (2013.01)

(58) Field of Classification Search
CPC .............. A61M 39/105; A61M 5/1408; A61M 25/0097; A61M 2206/20; A61M 5/1407; A61M 2039/1077; A61M 5/1413; A61M 5/1414; A61M 5/1418; A61M 2039/0027; A61M 39/10; A61M 2206/10; A61M 2206/11; A61J 1/10
See application file for complete search history.

(56) References Cited

U.S. PATENT DOCUMENTS

| 4,759,756 A | 7/1988 | Forman et al. |
| 6,508,791 B1 * | 1/2003 | Guerrero ............. A61M 5/1408 604/183 |
| 8,303,571 B2 * | 11/2012 | Kraushaar ........... A61M 39/105 604/533 |
| 2008/0262465 A1 | 10/2008 | Zinger et al. |
| 2012/0203204 A1 | 8/2012 | Briggs |

(Continued)

FOREIGN PATENT DOCUMENTS

WO  WO-2018082864 A1 * 5/2018 ........ A61M 16/1095

*Primary Examiner* — Amber R Stiles
*Assistant Examiner* — Avery Smale
(74) *Attorney, Agent, or Firm* — Armis IP Law, LLC

(57) ABSTRACT

An infusion coupling allows administration of IV drugs to a patient through an IV fluid line, and ensures that successive courses of medication are fully passed or flushed from the line to prevent mixing of incompatible drugs in the IV line. The infusion coupling includes a vessel body, and a plurality of branch inlets to receive medication through IV tubing connected to the inlets. The vessel body has a generally cylindrical shape such that each of the branch inlets is in fluidic communication with the interior volume for receiving the IV fluids for transport. The inlets are angled on the body of the infusion coupling. A transverse bar or obstruction extends across an interior diameter of the infusion coupling for disrupting a circular flow that can result in a vortex. Formation of a vortex can retain the infused medication in the infusion coupling and result in mixing with successive medication courses.

16 Claims, 7 Drawing Sheets

(56) References Cited

U.S. PATENT DOCUMENTS

2012/0203205 A1    8/2012  Briggs
2012/0220949 A1*  8/2012  Davies ................ A61M 5/3294
                                              604/191
2017/0290216 A1*  10/2017  Truitt .................... F16K 15/141

* cited by examiner

MULTI-LINE OPPOSED INLET INFUSION COUPLING

RELATED APPLICATIONS

This patent application claims the benefit under 35 U.S.C. § 119(e) of U.S. Provisional Patent App. No. 62/629,919, filed Feb. 13, 2018, entitled "MULTI-LINE OPPOSED INLET INFUSION COUPLING," incorporated herein by reference in entirety.

BACKGROUND

Medical, scientific and research environments often rely on flexible tubing for conveying fluids. IV (intravenous) fluids are often administered in medical contexts through flexible tubing to a needle or central line inserted into a bloodstream of a patient. Liquid medication is commonly infused to a patient through an intravenous (IV) line. Where more than one type of medication is needed, a multi-line connector or manifold may be used. Typically, a manifold includes a main liquid flow passage and a plurality of branch passages in fluid communication with the main passage. Intravenous liquid, such as saline, flows steadily through the main passage. Liquid saline is often administered to a patient with or without additional medication. When a need arises to introduce medication to the patient, the medication is introduced into the main passage through one or more of the branch passages.

A manifold type of connector for IV medications may be employed for several drugs in succession. Certain therapeutic courses, for example chemotherapy treatments, employ a plurality of different drugs in a single session. Conventional IV manifolds have one or more inlets for administering successive courses of medication. These medications combine with the IV saline stream in the manifold for patient delivery.

SUMMARY

An infusion coupling allows administration of IV drugs to a patient through an IV fluid line, and ensures that successive courses of medication are fully passed or flushed from the line to prevent mixing of incompatible drugs in the IV line. The infusion coupling includes a vessel body adapted to transport intravenous (IV) fluids, such that the vessel body has an outlet configured for coupling to the patient for introduction of the IV fluids. A plurality of branch inlets (inlets) receive medication from IV bags or bottles through a line (IV tubing) connected to the inlets. An interior cavity or volume in the vessel body is defined by a generally cylindrical shape such that each of the branch inlets is in fluidic communication with the interior volume for receiving the IV fluids for transport. The inlets are angled on the body of the infusion coupling based on a flow and current for reducing or eliminating a vortex effect from fluid flow, and may be opposed or inline. A transverse bar, crossmember or obstruction extends across an interior diameter of the infusion coupling for further disrupting a circular flow that can result in a vortex. Formation of a vortex can retain the infused medication in the infusion coupling and result in mixing with successive medication courses administered through the infusion coupling. Multiple infusion lines may converge at each inlet, thus providing 4 or 6 infusion connections into an infusion coupling with 2 inlets.

Configurations herein are based, in part, on the observation that infusion couplings are often used to merge IV lines carrying different medications to a patient using a common IV line, thus preventing a need for multiple needle injection points on a patient. Unfortunately, conventional infusion couplings suffer from the shortcoming that the intersecting flow caused by branch inlets into the common IV line can cause circular vortex currents that retain the medication in the infusion coupling. The retained medication increases the onset time until it reaches the patient, and the retained medication can mix with a subsequent medication also added through the same or other inlet ports, which may result in an incompatible mixing of medications. Accordingly, configurations herein substantially overcome the shortcomings of conventional infusion couplings by providing an angled inlet port and transverse crossmember that direct the flow of branch inlets out of the infusion coupling by mitigating vortex currents that retain fluid.

In further detail, the multi-line infusion coupler device includes a vessel body adapted to transport IV fluids and having an outlet configured for coupling to a patient IV line for introduction of the IV fluids, and at least one branch inlet disposed at an predetermined acute angle on the vessel body. An interior volume in the vessel body is coupled such that each of the branch inlets in fluidic communication with the interior volume for receiving the IV fluids for transport. Each of the branch inlets has an intake position defined by an orifice on an interior of the vessel body, such that the intake position and angle of each branch inlet is based on an onset time for fluidic transport from the orifice.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

One drawback to IV infusion couplings that operate as a manifold is that they typically have considerable "dead volume." As used herein, "dead volume" refers to interior space where liquid tends to collect and stagnate, particularly in response to a vortex created from the IV fluid flowing through the coupling. Stagnation can result in trapped fluid medication mixing with successive medications, or even when a single medication is administered, can result in less than the intended dosage of medication reaching the patient and/or extend the time it takes for the medication to reach the patient.

Figure 1:
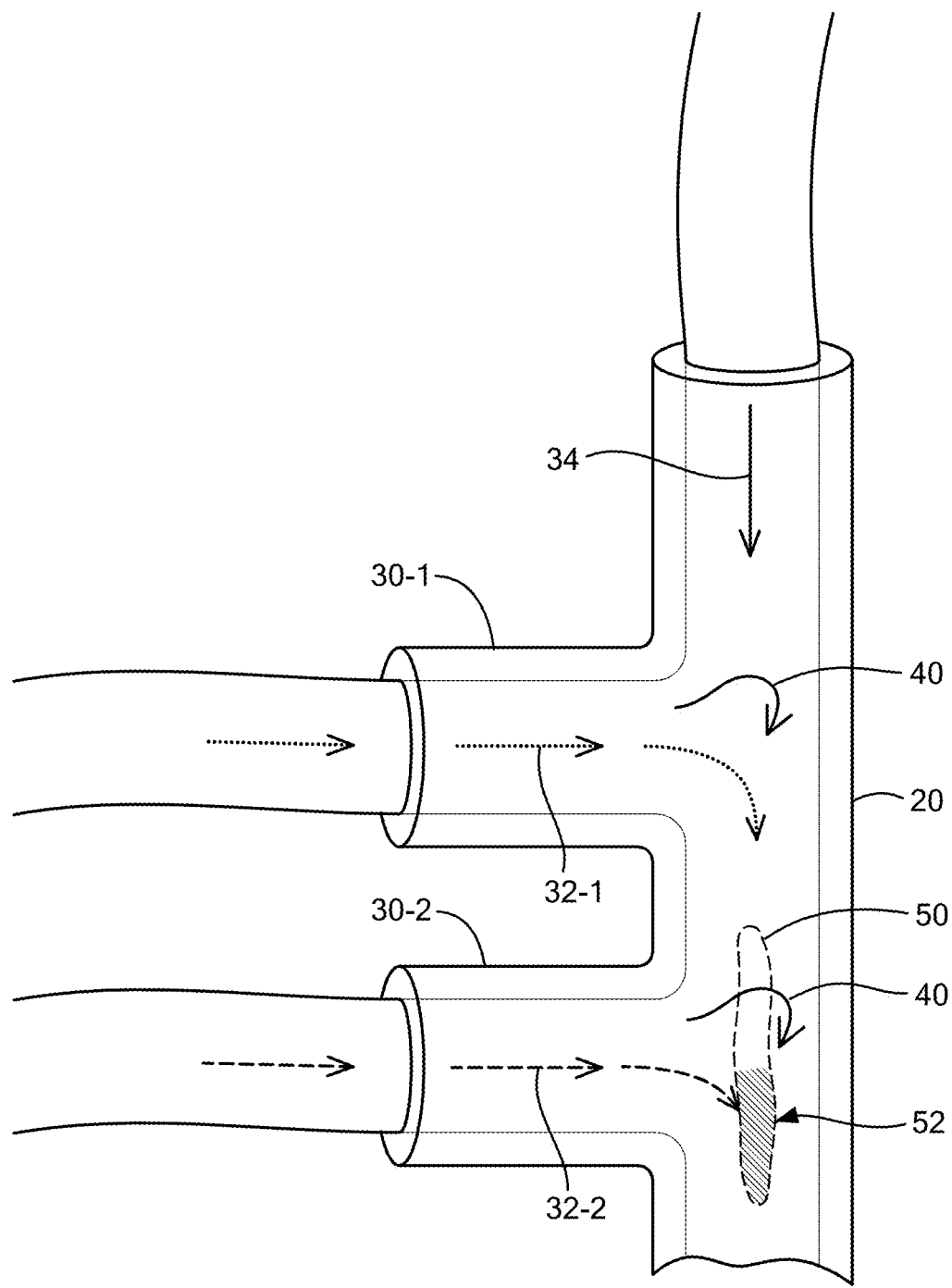
FIG. 1 is a prior art infusion coupling.

FIG. 1 is a prior art infusion coupling 10. Referring to FIG. 1, a conventional coupling 10 includes a body 20 and inlet ports 30-1, 30-2 (30 generally) for receiving a medication flow. The conventional ports 30 join the main vessel body 20 at a perpendicular or gently angled orientation. The medication 32-1, through port 30-1 and shown by dotted arrows, is incompatible with medication 32-2, through port 30-2 and shown by dashed arrows. A delivery IV flow 34 emanates from a delivery fluid source, typically a bag of IV saline. The flow through the perpendicular ports 30 can tend to cause a circular vortex 40 that results in retained fluid 50. Fluid from one source 30-1 causes an incompatible mixing 52 when medication 32-2 combines with retained fluid 50 from medication 32-2.

A particular conventional example, U.S. Pat. No. 8,303,571, to Kraushaar and Merchant, issued Nov. 6, 2012 and entitled "Multiple-line connective devices for infusing medication," shows branch inlet configurations including branch inlets aligned to merge with the main IV flow. This multiple-line connective device comprises a tubular body forming a main flow passage between an upstream end configured for coupling to a primary IV liquid source and a downstream end configured for connection to a device, such as a catheter, that can be coupled intravenously to a patient. There is no showing, teaching or disclosure of inlet orientation at an angle for mitigating residual droplets or traces of medication.

Figure 2:
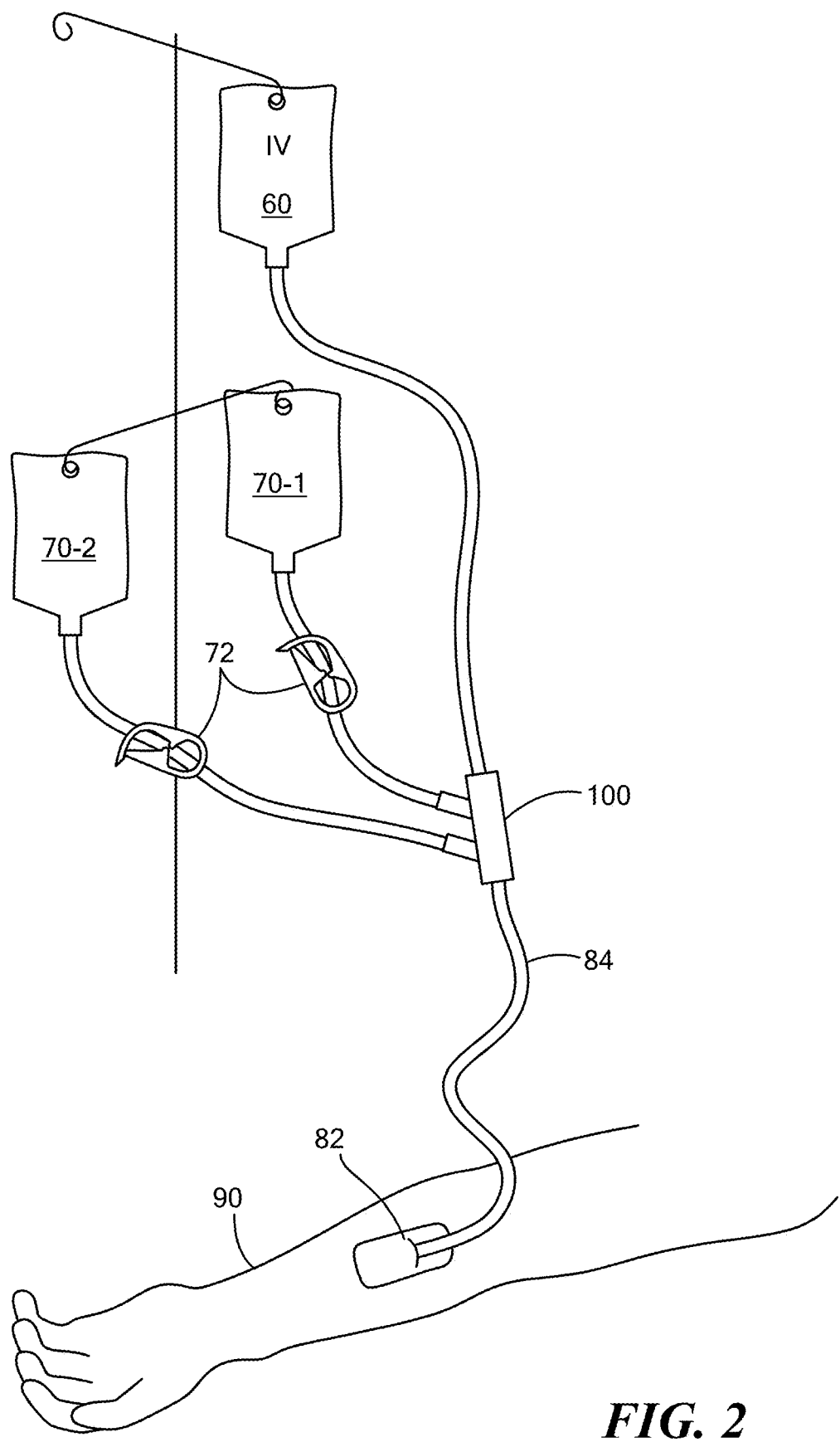
FIG. 2 is a context diagram suitable for use with configurations herein.

FIG. 2 is a context diagram suitable for use with configurations herein. Referring to FIG. 2, an IV fluid source such as an IV bag 60 is frequently employed to hydrate a patient 90 using saline or similar fluid. This often occurs independently of a need for additional medication, however the already established IV line 84 and injection site 82 provide a convenient conduit for medication. IV medication is typically dispensed from IV pouches 70-1, 70-2 (70 generally), which are smaller volume versions of the IV bag for the carrier saline. The infusion coupling 100 provides an introduction point of the medication into the main IV line 84 for patient 90 administration. Cutoff clamps 72 allow separate shutoffs for the respective IV pouches 70, typically by pinching the tubing line. If the medications in the pouches 70-1 and 70-2 are incompatible with each other, it is important that medication is flushed from the coupling 100 and delivered to the patient 90 before a subsequent medication pouch 70-2 is commenced.

Figure 3:
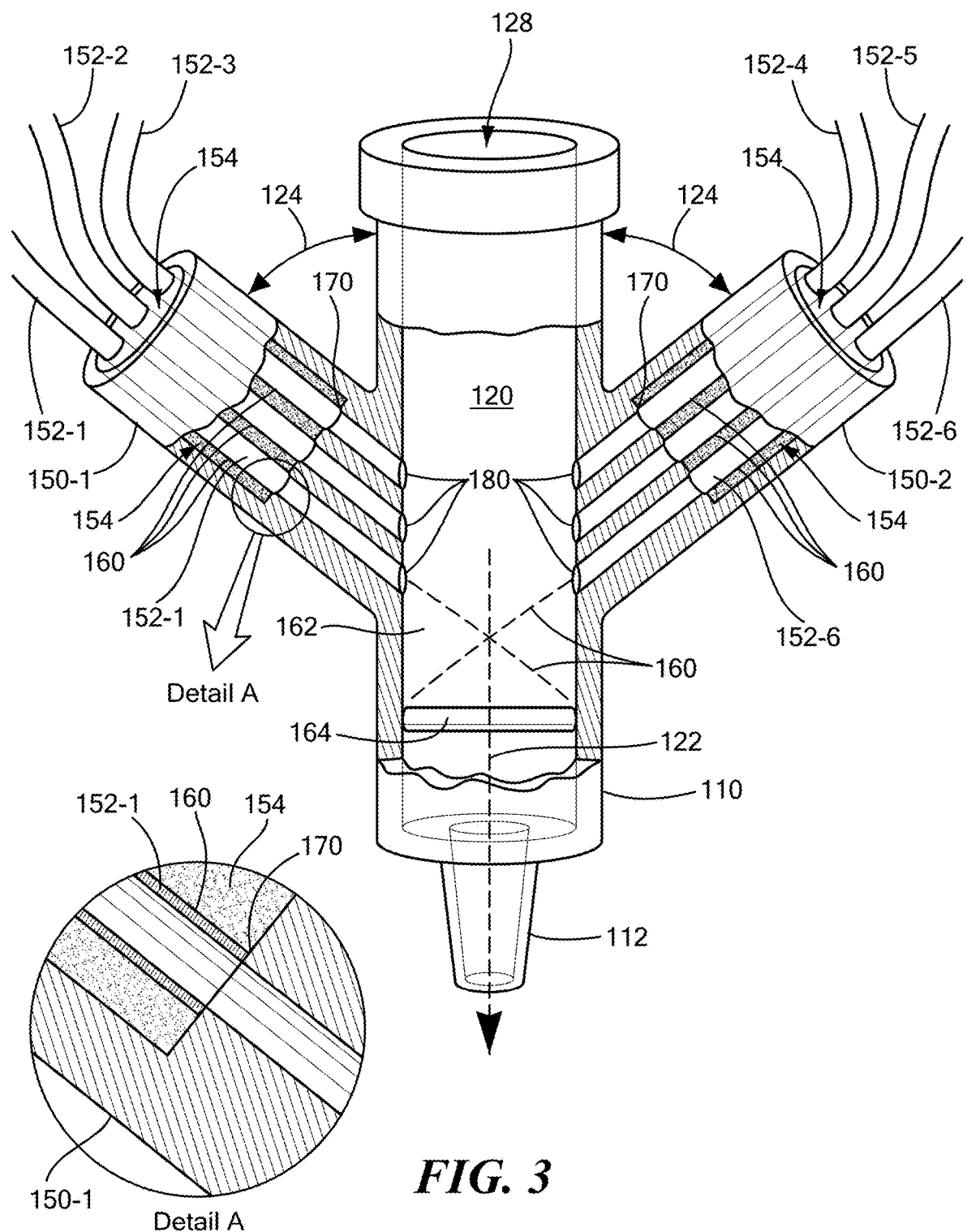
FIG. 3 shows an infusion coupling as defined herein.

FIG. 3 shows an infusion coupling as defined herein for illustrating a basic configuration. Referring to FIGS. 2 and 3, the infusion coupler device 100 as disclosed herein includes a vessel body 110 adapted to transport intravenous (IV) fluids. The vessel body has an outlet 112 configured for coupling to a patient IV line 84 for introduction of the IV fluids at a main IV inlet 128, and at least one branch inlet 150-1 . . . 150-2 (150 generally). Each of the branch inlets 150 are disposed at an acute angle 124 on the vessel body, typically in the range of 30°-45° from an axis through the circular diameter of the vessel body (i.e. the direction of fluid flow). The inlets 150 lead to an interior volume 120 in the vessel body 110, such that each of the branch inlets is in fluidic communication with the interior volume for receiving the IV fluids for transport. Each of the branch inlets 150 has an intake position defined by an orifice 180 on an interior of the vessel body 110. The intake position and angle of each branch inlet 150 is based on an onset time for fluidic transport from the orifice, discussed further in the configurations that follow. The angled branch inlets 150 may take a variety of orientation, such as opposed, in-line, and singular, depicted in the figures that follow.

In the cutaway view of the multiple line opposed inlet device for depicting the features defined herein. Continuing to refer to FIG. 3, the plurality of opposed branch inlets 150-1 . . . 150-2 (150 generally), are disposed on the vessel body 110 for receiving multiple sources of IV fluids from coupler liner 152-1 . . . 152-4 (152 generally). The interior volume 120 defines an axial direction 122 based on an exit path through the vessel body 110 towards the outlet 112, roughly centered in the substantially cylindrical shape of the vessel body 110.

The opposed branch inlets 150 are angled with respect to the axial direction 122 of the vessel body, and in a particular configuration, the branch inlets are angled 124 at 30 to 45° to the axial direction 122. Any suitable angle may be employed, such as between 30° to 60° from the axial direction 122 depending on a desired flow rate and resulting flow currents. The opposed branch inlets 150 define an intake position opposed from an intake position of another of the plurality of branch inlets on the vessel body. A common problem of multiple flow channels is for a vortex to be created at the of the branch inlets and the vessel body. Experimentation has shown that orienting the branch inlets at a 30 to 45 degree angle will help alleviate the vortex. The selection of an acute or "sharp" angle based on a flow rate and volume, along with the crossmember 164, provides a smooth flow for mitigating vortex currents.

Each of the branch inlets 150 may receive a plurality of coupler lines 152 for transporting the IV fluids, and are molded by shaping or filler 154 to maintain a closed system. The branch inlets 150 have individual channels or passages 160 along a substantially annular interior passage, where the branch inlet channels 160 are in fluidic communication with the interior volume 120 of the vessel body 110.

The individual branch channels 160 may have an elliptic or oval orifice 180 shaped in a downward direction promoting directional flow within 120 toward outlet 112. The oval outlet orifice 180 will be flush with the inside body of 110. A cap or additional inlet defines the top of the cylindrical shape of the vessel body 110. The branch inlets 150 include shoulders 170 molded into the interior of the branch inlets 150. The shoulders 170 have a depth based on a thickness of the coupler line 152 entering the branch inlet 150, such that the depth and thickness form a seamless union on an interior fluidic passageway defined by the insertion of the coupler line 152 against the shoulder 170.

The interior volume 120 includes a transverse bar 164 placed below the two most proximal inlet ports to reduce the impact of a vortex forming. This transverse bar 164 extends substantially across a diameter of the interior volume, and is adapted for directing fluid egress from the inlet orifices. Multiple and/or alternately positioned transverse bars 164 may also be employed. The transverse bar is adapted to disperse fluidic flow currents that would otherwise result in a vortex in the interior volume defined by the circular void in the vessel body 110 by protruding into a circular vortex current. Other orientations of the transverse bar 164 may also be achieved. The interior volume 120 having angled inlets 150 and the transverse bar 164 is adapted to reduce the onset time by elimination of a vortex in the interior volume. The vortex may otherwise cause fluid retention and result in an increased onset time. Medication remaining in the interior volume 120 may mix with a successive medication and cause incompatibility problems. The angle is based on a retention time during which fluids entering through the branch inlets remain in the interior volume, and serves to promptly expel medication through the outlet 112. There may also be a recession, indentation or groove around an interior of the vessel body 110 configured to receive the fluid flow from the orifices and directing the fluids from the interior volume to the outlet.

Channels, grooves or ridges 160 may be formed on an interior surface 162 of the vessel body 110 for directing fluid received from the branch inlets 150, and may extend from the inlets 150. The channels 160 are defined by recessed areas or other suitable structure or recession disposed for receiving and directing the IV fluids received from the branch inlets 150 such that the IV fluids travel through the vessel body 110 to the outlet 112 and cannot remain trapped in a void or cavity as a residual volume. A position and shape of the channels 160 serves to evacuate the received IV fluids from the interior volume 120, such that the channels 160 are disposed for preventing a residual volume of the IV fluids from remaining in the interior volume 120 following conclusion of a flow from the branch inlets.

Figure 4:
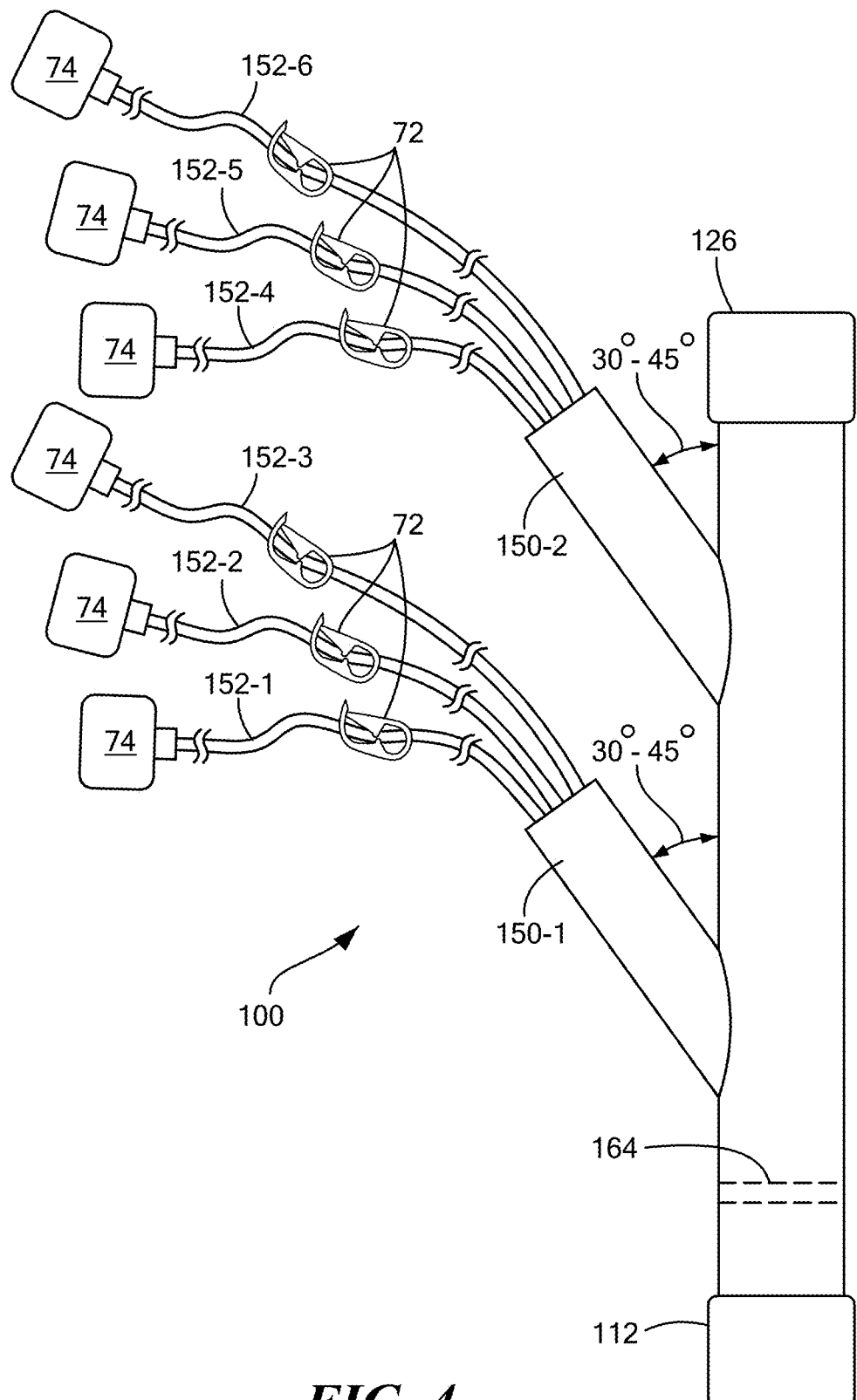
FIG. 4 shows an infusion coupling having multiple input lines.

FIG. 4 shows a configuration of the infusion coupling 100 having multiple input lines 152 aligned on a common side of the vessel body 110. Referring to FIGS. 2-4, as in the opposed configuration, each of the IV inlets 150 is configured for receiving IV transport fluid into the interior volume 120 and sourcing the outlet 112 to the patient. Each of the IV inlets 150 is connected to 3 coupler lines 152-1 . . . 152-6, therefore providing capability for 6 medications bags 70. Small bore tubing employed for the coupler lines 152 allows accommodation of 3 coupler lines 152 into each inlet 150, discussed further below in FIGS. 7A and 7B. A pinch clamp 72 on each coupler line 152 allows individual "valving" of each line. Each couple line 152 terminates in a female luer connector 74 for facilitating connection to the medication bags 70 via a male luer adapter. The main IV line connects to the inlet 128 also via a female luer connector 126.

In the device of FIG. 4, the infusion line coupling device 100 includes a cylindrical vessel body 110 having an IV (intravenous) input luer connection 126 and an IV output 112 adapted to receive an IV line for delivering IV fluids to a patient from an IV bag. An upstream branch inlet and a downstream branch inlet are disposed on the vessel body, such that each of the branch inlets joins the vessel body at a 30 degree-45 degree angle from perpendicular to a longitudinal axis through the vessel body. The branch inlets 150 are in fluidic communication with the interior volume 120 of the vessel body, and each branch inlet receives a plurality of small bore flexible tubes defining a plurality of coupler lines into each branch inlet. A female luer connector 74 at a distal end of each coupler line 152 is adapted to engage a medicinal pouch for patient delivery. A transverse crossmember 164 or bar across a diameter of the interior volume is generally perpendicular to the axis through the circular body and adapted for interference with circular vortex currents in the interior volume. Each branch inlet receives three coupler lines and the upstream and downstream branch inlets are oriented in parallel.

Figure 5:
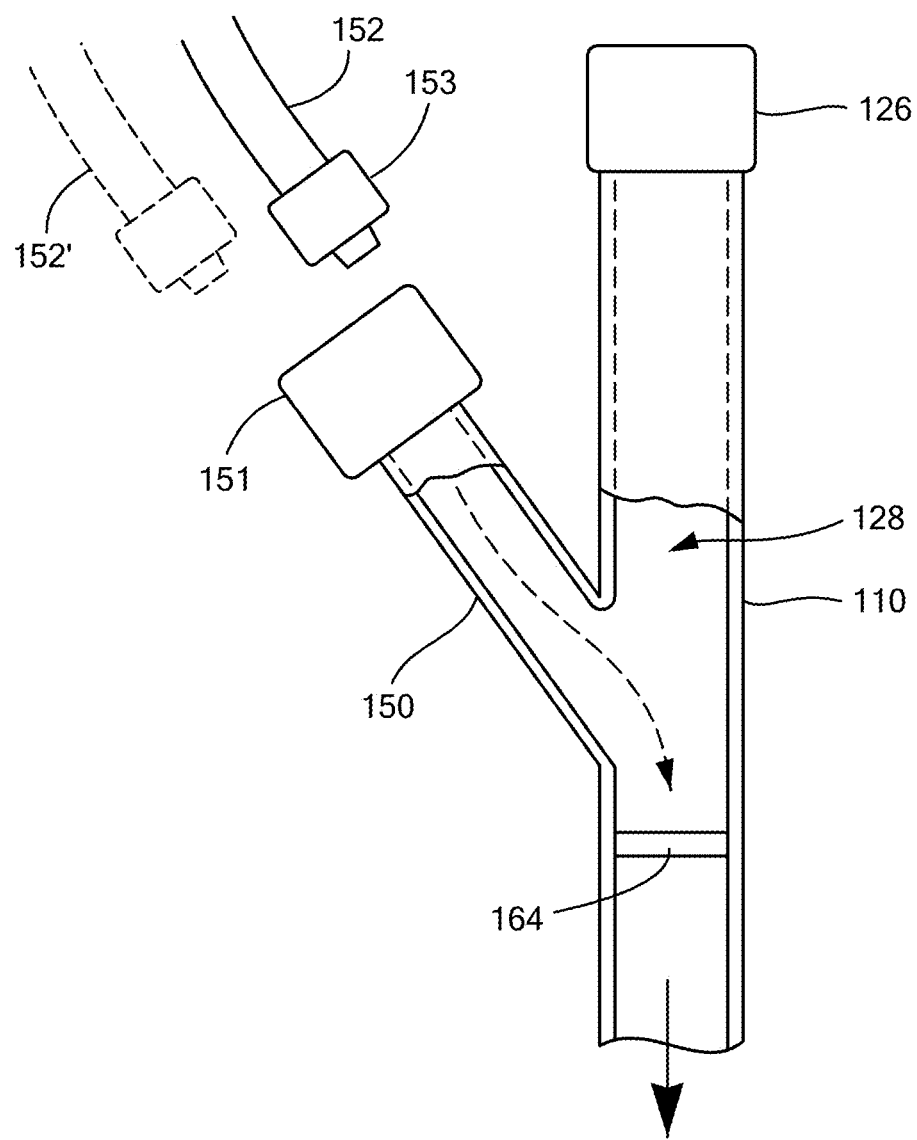
FIG. 5 shows fluidic flow through an infusion coupling as in FIGS. 3 and 4.

FIG. 5 shows fluidic flow through an infusion coupling as in FIGS. 3 and 4. Referring to FIGS. 2-5, FIG. 5 is another configuration having a single branch inlet 150. In general, the IV inlet 128 is defined by an upper perimeter of the vessel body 110, and the outlet 112 is defined by a lower perimeter for passing fluid received at the IV inlet. The infusion coupling 100 has the appearance of a vessel body 110 depicted by a generally cylindrical shape and the upper perimeter and lower perimeter are defined by a diameter of opposed circular ends of the cylinder. The upper perimeter typically has a female luer connection 126 receptive to a male luer adapter, as are common in the industry for providing a leak-free engagement. Similarly, the branch inlet 150 has a female luer connector 151, and is receptive to coupler lines 152 having male luer adapters 153. Medication changes in the single input configuration are achieved by disconnecting the male luer 153 and attaching a second medication via another coupler line 152' to the female luer connector 151. It should be apparent that the IV inlet has a greater cross section than the branch inlets and is operable for a greater fluidic volume than the branch inlets, thus providing appropriate dilution of the delivered medication.

Figure 6C:
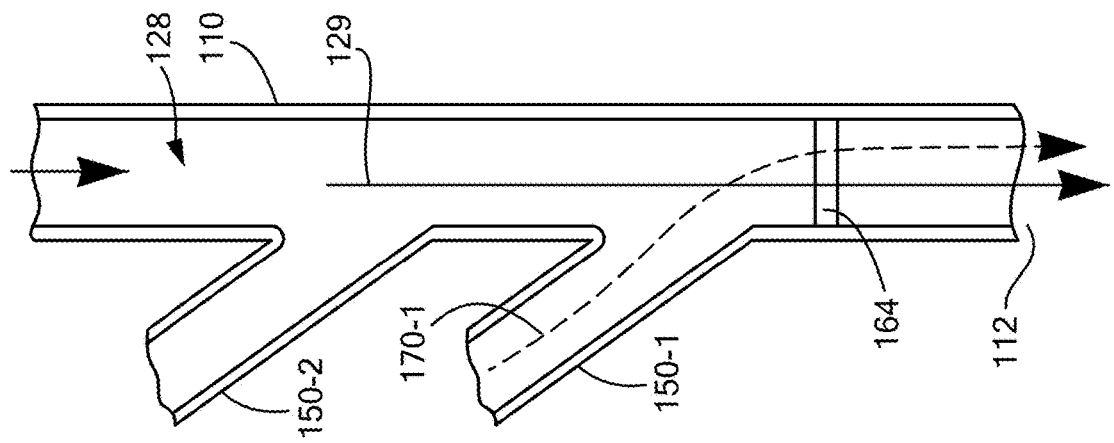
FIGS. 6A-6C show separation of incompatible medications in the infusion coupling of FIGS. 3-5.
Figure 6B:
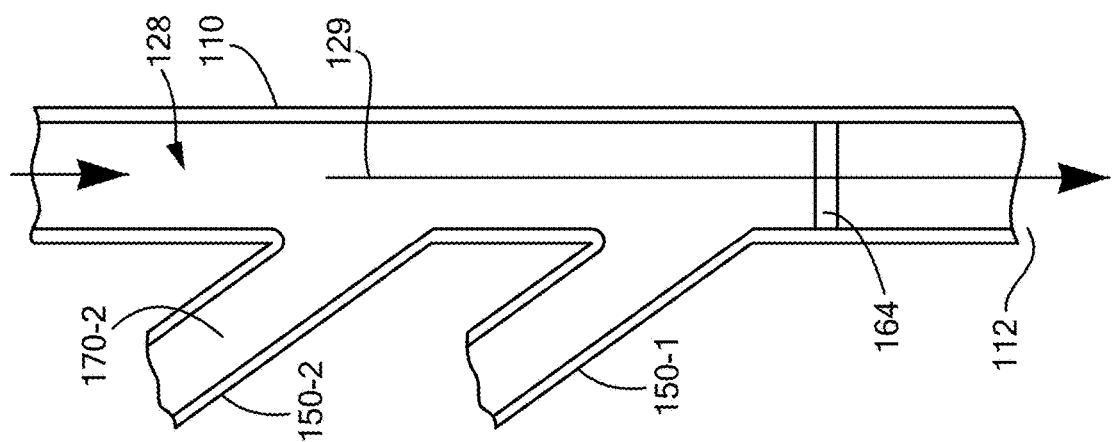
Figure 6A:
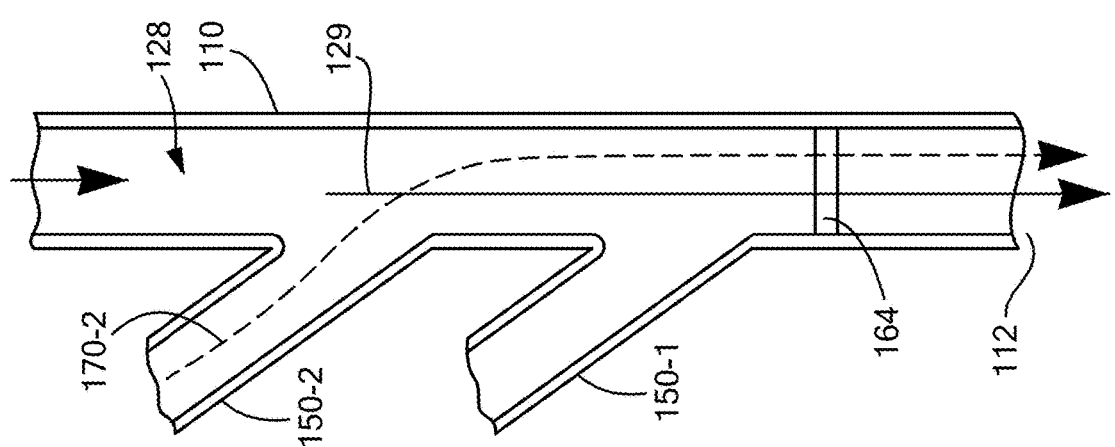

FIGS. 6A-6C shows separation of incompatible medications in the infusion coupling of FIGS. 3-5. Referring to FIGS. 2-6C, inlet 150-2 carries a medicinal stream 170-2, such as from an IV pouch 70-2. The medicinal stream 170-2 combines with the saline stream 129 for delivery via the outlet 112. Following dispensation of a complete dose and termination of the medicinal stream 170-2, the saline stream 129 flushes the line of any residual medication, shown at FIG. 6B. In FIG. 6C, a different medicinal stream 170-1 is commenced through inlet 150-1, and combines with only a pure saline stream 129 for outlet 112 delivery. As indicated above, the vortex can persist along the housing 110, therefore in conventional approaches a medicinal flow from an upstream or downstream inlet 150 could cause a residual volume that presents a mixing hazard with a subsequent medicinal stream. The inlets 150 may be disposed at a distance from the output 112 based on a time for the IV flow 129 to transport the medication out of the vessel body 110.

Figure 7B:
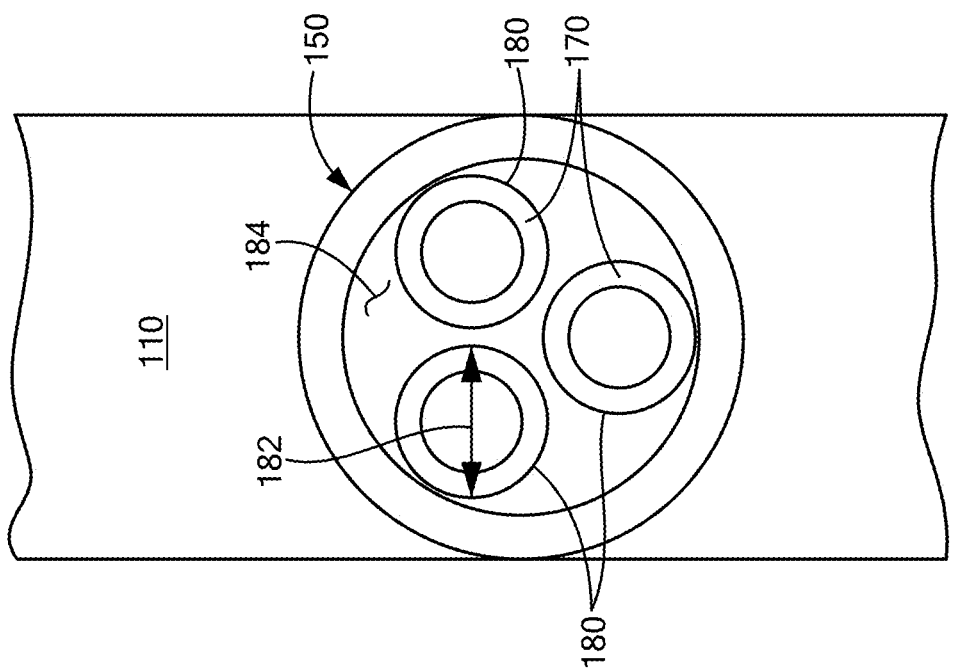
FIGS. 7A-7B show multiple inlet lines in an infusion coupling of FIGS. 3-5.
Figure 7A:
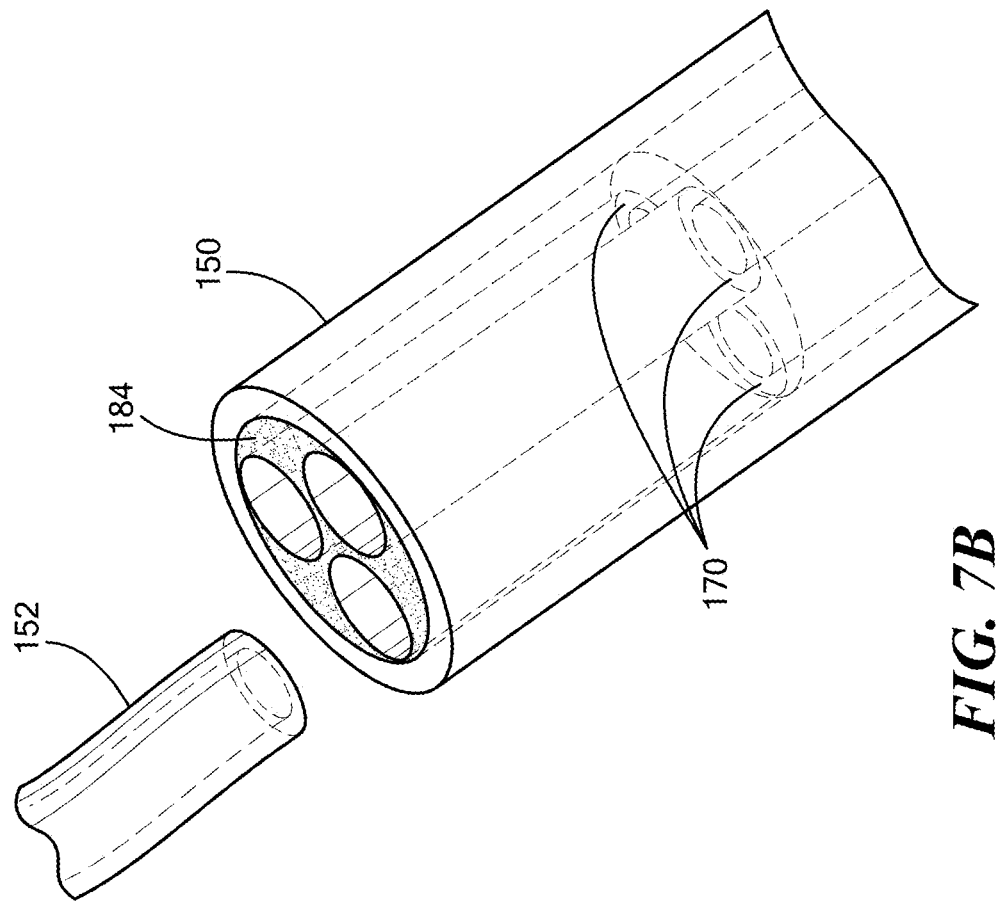

FIGS. 7A-7B show multiple inlet lines in an infusion coupling of FIGS. 3-5. A plurality of flexible tubes may connect to each branch inlet 150, and each flexible tube may have a luer connector for engaging a medicinal source to receive a medicinal flow into the interior volume 110. Multiple coupler lines 152 of small bore tubing may combine into each inlet 150. This facilitates connection to multiple IV pouches 70. The small bore tubing engages a plurality of tubing receptacles 180 within the branch inlet 150, such that the tubing receptacles 180 have a circular diameter 182 based on the flexible tubing for frictional engagement with tubing. A molding 184, or filler, occupies around an interior of the branch inlets 150. The molding 184 occupies voids between the inserted flexible tubes for defining a fluidically sealed engagement between the flexible tubes and the branch inlet. Any suitable fusing, molding or adhesive may be employed to secure the coupler lines in the branch inlet 150. The molding may be part of the fabrication of the connector 100, or may be added as the coupler lines 152 are inserted. The inlets 150 have a shoulder 170 corresponding to an insertion depth of the inserted flexible tubes. The flexible tubes are of a small bore such that the inlet can accommodate at least three or 4 parallel tubes for insertion as the coupler lines 152.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. An infusion line coupling device, comprising:
   a cylindrical vessel body having an IV (intravenous) input and an IV output adapted to receive an IV line for delivering IV fluids to a patient from an IV bag;
   a plurality of branch inlets on the vessel body, each branch inlet of the plurality of branch inlets entering the vessel body at an intake position, each branch inlet of the plurality of branch inlets opposed from another branch inlet of the plurality of branch inlets, at least one branch inlet of the plurality of branch inlets having a respective intake position opposed across a diameter of the vessel body from an intake position of the respective opposed branch inlet, each branch inlet of the plurality of branch inlets disposed at an acute angle to a fluid flow through the vessel body, each of the branch inlets joining the vessel body at a 30 degree-45 degree angle from the fluid flow defining a longitudinal flow axis through the vessel body and in fluidic communication with an interior volume of the vessel body;

each branch inlet of the plurality of branch inlets receiving a plurality of small bore flexible tubes defining a plurality of coupler lines into each branch inlet of the plurality of branch inlets;

a transverse bar extending diametrically across a diameter of the vessel body and perpendicular to the longitudinal flow axis through the vessel body, and disposed downstream of the plurality of branch inlets to the vessel body, the transverse bar adapted for interference with circular vortex currents in the interior volume.

2. The device of claim 1 wherein the interior volume is adapted to reduce an onset time for fluidic transport by elimination of a vortex in the interior volume, the vortex causing fluid retention and resulting in an increased onset time.

3. The device of claim 1 wherein the angle is based on a retention time during which fluids entering through the plurality of branch inlets remains in the interior volume.

4. The device of claim 1 further comprising an IV inlet on the vessel body, the IV inlet configured for receiving IV transport fluid into the interior volume and sourcing the IV output to the patient.

5. The device of claim 4 wherein the IV inlet is defined by an upper perimeter of the vessel body, the IV output defined by a lower perimeter for passing fluid received at the IV inlet.

6. The device of claim 5 wherein the vessel body is generally cylindrical and the upper perimeter and lower perimeter are defined by a diameter of opposed circular ends of the cylinder.

7. The device of claim 1 wherein each flexible tube of the plurality of flexible tubes has a connector for engaging a medicinal source to receive a medicinal flow into the interior volume.

8. The device of claim 7 further comprising a plurality of tubing receptacles within the plurality of branch inlets, the tubing receptacles having a circular diameter based on the flexible tubes for frictional engagement with the flexible tubes.

9. The device of claim 7 further comprising a molding around each branch inlet of the plurality of branch inlets, the molding occupying voids between the inserted flexible tubes and defining a fluidically sealed engagement between the flexible tubes and the respective branch inlet.

10. The device of claim 7 further comprising a shoulder corresponding to an insertion depth of the inserted flexible tubes, the flexible tubes being small bore such that each branch inlet of the plurality of branch inlets can accommodate at least three parallel tubes.

11. The device of claim 1 further comprising a ridge around an interior of the vessel body, the ridge configured to receive fluid from the plurality of branch inlets and direct the fluids from the interior volume to the IV output.

12. The device of claim 1 further wherein the plurality of branch inlets are disposed at a distance from the IV output based on a time for the IV fluids to transport a medication out of the vessel body.

13. The device of claim 1 wherein the plurality of branch inlets each receives three coupler lines.

14. The device of claim 1 wherein the opposed branch inlets of the plurality of branch inlets are defined by a diameter across an interior of the vessel body.

15. A method for delivering IV medication, comprising:
defining a cylindrical vessel body having an interior volume, the vessel body adapted for connection to IV (intravenous) delivery lines;
forming a plurality of branch inlets on a side of the vessel body, the plurality of branch inlets in fluidic communication with the interior volume, each branch inlet of the plurality of branch inlets entering the vessel body at an intake position, at least one branch inlet of the plurality of branch inlets opposed from another branch inlet of the plurality of branch inlets, at least one branch inlet of the plurality of branch inlets having an intake position opposed across a diameter of the vessel body from a respective intake position of the opposed branch inlet, each branch inlet of the plurality of branch inlets having an angle in a range between 30-45 degrees from a longitudinal axis through the vessel body;
attaching a plurality of connector lines to each of the plurality of branch inlets, the connector lines having a smaller bore than the branch inlets and combining in an interior of a respective branch inlet of the plurality of branch inlets;
disposing a transverse bar diametrically across a diameter of the vessel body and having an axis perpendicular to a longitudinal flow axis through the vessel body, the transverse bar disposed downstream of the opposed branch inlets to the vessel body, the transverse bar defining an obstruction for interference with circular vortex currents; and
attaching a luer connector to each of the connector lines for engaging a medicinal pouch.

16. The method of claim 15 wherein the transverse bar extends perpendicularly from an interior of the vessel body for extending across a diameter of the interior of the vessel body.

* * * * *